United States Patent [19]

Turner et al.

[11] Patent Number: 4,673,398
[45] Date of Patent: Jun. 16, 1987

[54] SUCTION DEVICE FOR USE WITH TRACHEOSTOMY TUBE

[76] Inventors: Kenneth R. Turner, 36 Orchard Rd., Akron, Ohio 44313; James A. Ashe, P.O. Box 619, Geneva, Ohio 44041

[21] Appl. No.: 809,292

[22] Filed: Dec. 16, 1985

[51] Int. Cl.$^4$ .............................................. B65B 3/04
[52] U.S. Cl. .................... 604/264; 604/268; 604/902; 604/73; 604/275
[58] Field of Search ............ 128/207.14; 604/73, 604/76, 93, 264, 266, 268, 275, 276, 280, 283, 902

[56] References Cited

U.S. PATENT DOCUMENTS 3,430,628  3/1969  Wiggins ........................ 604/264
4,022,218  5/1977  Riddick ........................ 604/266
4,182,385  1/1980  Williamson .................... 604/73
4,510,933  4/1985  Wendt et al. ................. 128/207.14

Primary Examiner—C. Fred Rosenbaum
Assistant Examiner—Sherri Vinyard
Attorney, Agent, or Firm—Oldham, Oldham & Weber Co.

[57] ABSTRACT

Suction device for use with a tracheostomy tube to remove matter from the upper respiratory tract of a patient. The suction device is essentially tubular and open at both ends, and comprises a bulb near one end and a tubular portion which extends from the bulb to the other end. To use, one connects the end remote from the bulb to a source of vacuum and inserts the bulbous end of the suction device into the end of a tracheostomy tube which is outside the patient's body. The suction device can be used with tracheostomy tubes of different sizes, and is used in place of a catheter.

12 Claims, 5 Drawing Figures

SUCTION DEVICE FOR USE WITH TRACHEOSTOMY TUBE

TECHNICAL FIELD

This invention relates to a device for removing matter from the upper respiratory tract of a patient. More particularly, this invention is a suction device used primarily for suctioning a tracheostomy patient with the use of vacuum aid.

BACKGROUND ART

Tracheostomy tubes are commonly used to aid patients with breathing and/or respiratory problems. An opening is established in the throat and a tracheostomy tube is inserted to maintain the opening and to act as the passageway from the respiratory tract to the outside of the body, thus bypassing the nose and mouth. Conditions which indicate use of the tracheostomy tube are blockages in the upper respiratory tract, that must be bypassed, or a problem with the lungs. When matter is congesting in the lungs or upper respiratory tract, it is necessary to assist the patient in expelling the foreign material.

In present technology, a normal saline solution or other mucolytic expectorant is introduced into the patient's trachea via the tracheostomy tube. The saline solution serves to break up the phlegm or other matter, and also causes the patient to cough. A catheter is then inserted through the tracheostomy tube into the body approximately $4\frac{1}{2}$ inches, or until an obstruction is reached. The catheter in the tracheal device then seeks to retrieve the unwanted matter, which is drawn away by some suctioning machine.

There are several problems with the catheter and it use. When the catheter is introduced into the body, the possibility exists that the device will come into contact with the tissues of the trachea, causing trauma and injury. In addition, once inside the trachea, the tube may come into contact with a nerve which may cause a seizure. Introduction of such a device inside the body also presents a possibility of infection. The method taught by the prior art, involving the use of normal saline or some other mucolytic expectorant to cause the patient to cough and expectorate the phlegm, causes matter to be expelled beyond the area of the catheter and suction thus creating potential infection to others.

A further disadvantage of the catheter is that only a low suction is available to assist the patient. Finally, use of the catheter generally requires the presence of qualified allied health professionals. Such a person is generally available only in a hospital or skilled nursing home center.

DISCLOSURE OF THE INVENTION

It is an object of this invention to provide a suction device which will replace a suction catheter for removing matter from the upper respiratory tract of a patient.

It is a further object of this invention to provide a suction method for use in conjunction with a vacuum aid to remove matter from the upper respiratory tract of a patient through the tracheostomy tube.

It is a still further object of this invention to provide a suction device which is less hazardous to use than a suction catheter and which will permit more effective suctioning.

A still further object of this invention is to provide a suction device by which a qualified health professional or lay person can effectively suction matter from the upper respiratory tract of a patient having a tracheostomy tube.

A still further object of this invention is to provide a suction device which does not require insertion of a catheter into the body, thus virtually eliminating the possibility of trauma, injury, infection or seizures.

It is a still further object of this invention to provide a suction device whose design increases the amount of suction available to assist the patient and in addition, allows direct access to acquiring a specimen of the matter which cannot be provided by the present suction catheter.

The suction device of this invention is an open ended essentially tubular structure comprising a hollow bulb near one end thereof and a tubular portion extending from said bulb, the bulbous end being adapted for insertion into the end of a tracheostomy tube which is outside the patient's body.

BEST MODE FOR CARRYING OUT THE INVENTION

Figure 2:
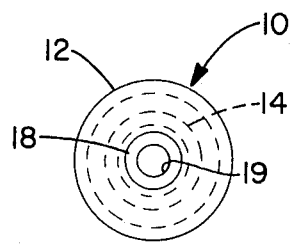
FIG. 2 is an end view of the suction device as seen from the end near the bulb.
Figure 3:
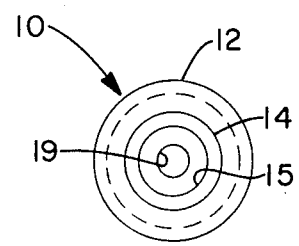
FIG. 3 is an end view of the suction device as seen from the end remote from the bulb.

A preferred form of the suction device of this invention will now be described with respect to the drawings and especially FIGS. 1-3.

Figure 1:
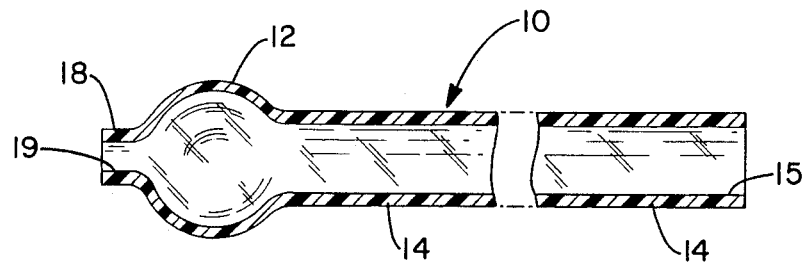
FIG. 1 is a longitudinal sectional view, partly in elevation, of a preferred form of the suction device of this invention.

Referring now to FIG. 1, 10 indicates generally a suction device according to this invention. Suction device 10 is an elongated generally tubular structure which is open at both ends. This device may be made of glass or a thermoplastic material (e.g. polyethylene). Suction device 10 comprises a hollow spherical bulb 12 near one end thereof, and a hollow cylindrical or tubular portion 14 extending from the bulb 12 to the other end of suction device 10, i.e. the end remote from bulb 12. The interior of tubular portion 14 is in communication with the interior of hollow bulb 12.

Tubular portion 14 is open at its outer end. The diameter of this opening 15 and the inside diameter of tubular portion 14 are the same. Tubular portion 14 is of appreciable axial length; typically the axial length of tubular portion 14 exceeds the diameter of bulb 12. The outer end of tubular portion 14 is adapted to be attached to a source of vacuum as will be described with reference to FIG. 4.

Extending from bulb 12 in axial alignment with tubular portion 14 is a projection or shank 18 of very short axial length. Projection 18 has an opening 19 at its outer end. Projection 18 and opening 19 together form a passageway from the exterior of suction device 10 to the interior of bulb 12. Opening 19 is of smaller diameter than opening 15 at the outer end of tubular portion 14. Since opening 19 is smaller than opening 15, the suction at opening 19 is greater than the suction at opening 15. Thus, by making opening 19 smaller than opening 15, one attains a greater suction at opening 19 and a higher velocity of air and aspirated material (phlegm, for example) than one would achieve if the two openings, 15 and 19, were of the same diameter. Second cylindrical portion 18 may be omitted, in which case an opening may be provided in bulb 12 diametrically opposite the intersection between bulb 12 and tubular portion 14.

Both the outside and inside surfaces of suction device 10 are rounded at the intersections between bulb 12 and tubular portions 14 and 18.

Bulb 12 is spherical, so that undesirable vibrations or harmonics which would be encountered with an ellipsoidal bulb are avoided. A further advantage of a spherical bulb is that the bulb can be inserted at any angle into the end of a tracheostomy tube, as will be explained more fully hereafter. Bulb 12 is considerably larger in diameter than either cylindrical portion 14 or cylindrical portion 18. Cylindrical portion 14 is generally larger in diameter than cylindrical portion 18. A representative suction device according to this invention may have the dimensions shown in Table I below. All dimensions are in inches.

TABLE I

| Item | Size (inches) |
| --- | --- |
| Length of suction device 10 | 3.0 |
| O.D. of bulb 12 | 0.625 |
| I.D. of bulb 12 | 0.565 |
| O.D. of tubular portion 14 | 0.3150 |
| I.D. of tubular portion 14 | 0.1969 |
| O.D. of projection 18 | 0.212 |
| Diameter of opening 19 | 0.125 |

In the above table I.D. and O.D. are inside diameter and outside diameter, respectively.

It is to be understood that both the absolute and the relative dimensions of the various portions of the suction device may be varied.

Suction device 10 may be made of either glass or a pharmaceutically acceptable (i.e. non-toxic) plastic. Glass suction devices should be made from a high quartz glass, e.g. a borosilicate glass; soda lime glass should be avoided. Plastic suction devices are preferably made of a transparent or translucent plastic.

Glass suction devices according to this invention can be made as follows:

The starting glass is a borosilicate glass, such as "Kimble KG-33", made by Owens-Illinois Co., Toledo, Ohio, in the form of tubing with a wall thickness of 0.15 mm (0.0585 inch) and an inside diameter of 0.1969 inch. This glass has a working point of 1260° C., a softening point of 827° C., and an annealing point of 565° C., according to literature published by the manufacturer. The tubing is cut into 16 inch lengths. One end of a length is attached to an air pressure source. The length is preheated to above the working point (1260°) and the other end is sealed by fusion. Glass gathers at the sealed end. Meanwhile, a vertically oriented carbon mold having two identical mating halves is preheated to about 750°-800° F. (approximately 400°-425° C). The two halves when placed together have mating cavities forming a sphere of the desired diameter (0.625 inch) and two axially aligned cylindrical passageways, 0.312 inch and 0.212 inch in diameter respectively, one on each side of the sphere. (These diameters are the same as the respective outside diameters of tubular portion 14 and projection 18). The preheated length of glass tubing is placed into the preheated mold with the sealed end slightly below the center of the spherical cavity and the unsealed end extending above the mold. Then about 20–40 psig (about 1.3–2.7 atmospheres) of air pressure is applied to form bulb 12, and pressure is stopped when molten glass blows into the narrower passageway. Then the hot glass is removed from the mold, excess glass roughness or "flash" at the shank end (the end which becomes projection 18) is removed, and cooled in a cooling box which is neither heated nor cooled. The cooling box is rectangular in cross section, open at both ends, and has a rod extending its entire length. A plurality of hot glass suction devices are placed in the cooling box with the respective bulbs touching the next adjacent suction device on either side; the bulbs are supported by the cooling box rod so that the only portions of a suction device which touches any other surface are a portion of each suction device at the bulb and a portion of each device at the open end thereof. Each suction tube remains in the cooling box for about 6 hours. Hot glass tubes are loaded at one end of the box, and cooled glass tubes are removed from the other end. The cooled glass tube is cut to desired length (about 3 inches), is flame polished and annealed by heating to annealing temperature (550° F. or about 288° C.) for one hour. A high speed (3450 RPM) cutting wheel designed for cutting tungsten carbide saw blades is the preferred cutting tool. The remaining length of glass tubing (approximately 13 inches) is then sealed at one end and fabricated as described above. This is repeated until the entire length of glass tubing is used. In the absence of breakage, 5 suction devices are obtained from each 16 inch length of glass tubing.

Plastic suction devices can be formed by conventional blow molding techniques.

Figure 4:
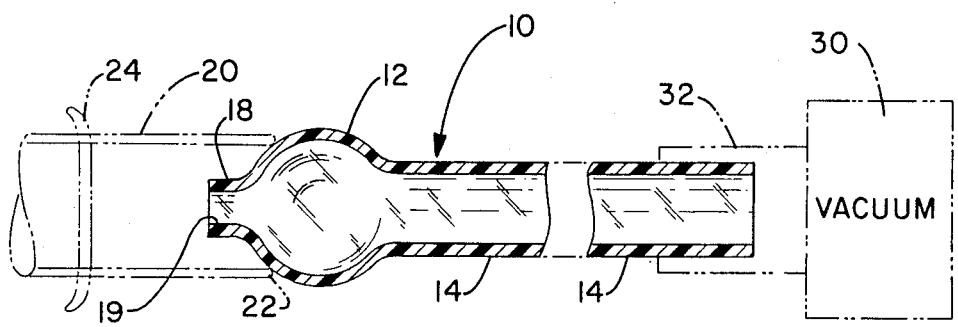
FIG. 4 is an elevational view of an assembly comprising a suction device (shown in longitudinal section) of this invention in combination with a tracheostomy tube and a source of suction, the latter two being shown in phantom lines and only a portion of the tracheostomy tube being shown.
Figure 5:
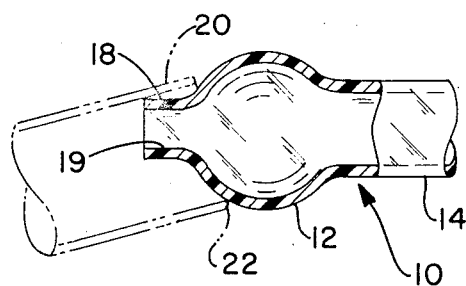
FIG. 5 is a view of a portion of the assembly shown in FIG. 4, the suction device and the tracheostomy tube being shown at an angle with respect to each other.

Use of the suction device 10 of this invention with a tracheostomy tube will now be described with reference to FIG. 4. Referring now to FIG. 4, the bulbous end of suction device 10 is inserted into the end 22 of a tracheostomy tube 20 which is outside the patient's body, forming a thin, annular passage for air between the bulb 12 and the end 22 of the tracheostomy tube 20. A tight seal is not formed because both the suction device 10 and the tracheostomy tube 20 are hard materials. It is neither essential nor desirable to form an airtight seal, since considerable suction through opening 19 can be attained without an airtight seal. It is not necessary to insert the suction device 10 in axial alignment with the tracheostomy tube 20, as shown in FIG. 4; instead, the suction device can be inserted quickly, with the axes of the suction device 10 and the tracheostomy tube at an angle with respect to each other, as shown in FIG. 5. The dot-dash lines in FIG. 4 show the tracheostomy tube 20 in axial alignment with suction device 10, and the dotted line in FIG. 5 show the axis of suction device 10 and tracheostomy tube 20 at an angle with respect to each other. The spherical shape of bulb 12 makes this possible. Tracheostomy tube 20 also has a collar 24, which is against the patient's throat when the tube is inserted into a patient's body.

A vacuum source 30 is connected to the other end of suction device 10 (i.e. the end which is remote from bulb 12). Vacuum source 30 may include flexible tubing 32 for connection to cylindrical portion 14 of suction device 10. Vacuum source 30 may be a rubber bulb, or a small electrically driven laboratory vacuum pump, or other suitable suction-producing device. The source 30 need not be capable of producing a high vacuum.

To remove matter from a patient's upper respiratory tract, the suction device 10 is brought in contact with a tracheostomy tube 20 and is connected to a vacuum source 30 as shown in FIG. 4, and suction is applied by vacuum source 30. Application of suction may begin either before or after the bulb 12 of the suction device is inserted into the end of the tracheostomy tube 20. When a power suction device is used, application of suction preferably commences before the device is inserted into the tracheostomy tube. Any matter which is removed from the patient is caught in bulb 12.

Tracheostomy tube 20 and vacuum source 30 are shown in phantom lines and only the portion of tracheostomy tube 20 which is outside the patient's body is shown since the details of tube 20 and vacuum source 30 do not form part of the present invention.

This invention is especially beneficial in situations where a source of electricity is not available, as in a power failure, in an emergency, or in a military on-field situation. Under these circumstances, a simple squeeze bulb can be used.

A suction device according to this invention may be used with different sizes of tracheostomy tubes. The diameter of bulb 12 must be larger than the inside diameter of the outside end of the tracheostomy tube for effective use and the outside diameter of cylindrical portion 18 must be less than the inside diameter of the tracheostomy tube to permit insertion. Since bulb 12 is usually much larger in diameter than cylindrical portion 18, the suction device 10 may be used with different sizes of tracheostomy tubes. Tracheostomy tubes range in inside diameter from about 0.158 inch (4 mm) (for an infant) to about 0.433 inch (11 mm) (for an adult). A suction device having the dimensions given above can be used with the full range of tracheostomy tubes.

The suction device 10 is capable of producing stronger suction than the usual catheter tube. First, bulb 12 acts as a vacuum reservoir to increase the amount of suction available. Second, application of a given suction or negative pressure in tubular portion 14 results in a much greater negative pressure at opening 19 because opening 19 is smaller in diameter than tubular portion 14. The stronger suction is useful in withdrawing matter which cannot be removed with the aid of a catheter.

A further advantage of the suction device of this invention is that it is safer to use than a catheter. Hazards which may attend the use of a catheter, such as trauma, injury and seizure, have been pointed out earlier. None of these hazards are present when the present suction device is used, because this device is not introduced into the human body.

While in accordance with the patent statutes, a preferred embodiment and best mode has been presented, the scope of the invention is not limited thereto, but rather is measured by the scope of the attached claims.

What is claimed is:

1. A suction device adapted to be inserted into the end of a tracheostomy tube which is outside the patient's body for removing matter from the upper respiratory tract of said patient, said suction device being inflexible, essentially tubular and open at both ends and comprising:

a hollow spherical bulb near one end thereof, said bulb having an outside diameter larger than that of said tracheostomy tube;

a tubular portion of appreciable axial length extending from said bulb and having an opening at its outer end, the diameter of said tubular portion being substantially less than the diameter of said bulb, and a hollow projection extending from said bulb in a direction opposite to that of said tubular portion and having an opening at its outer end, said last-mentioned opening being smaller in diameter than the opening at the outer end of said tubular portion, the outside diameter of said hollow projection being less than the inside diameter of said open end of said tracheostomy tube, the bulbous end of said suction device being adapted for insertion into the end of the tracheostomy tube which is outside the patient's body so that said bulb is against the end of said tube and said projection is in communication with said tube, the axial length of said projection being substantially less than the diameter of said hollow spherical bulb, so that said suction device can be inserted with the axes of the suction device and the tracheostomy tube at an angle with respect to each other, the outer end of said tubular portion being adapted to be attached to a source of vacuum.

2. A method for making a suction device as claimed in claim 1 said method comprising:

(a) sealing one end of a glass tube;

(b) inserting said tube into a two-piece mold having a spherical cavity and axially aligned cylindrical passageways extending in either direction from said spherical cavity, one of said passageways being at least as large in diameter as said tube and the other passageway being smaller in diameter than said tube being inserted so that the closed end abuts against the wall of said spherical cavity in proximity with the intersection of said cavity with the smaller passageway;

(c) applying pressure to the open end of said tube to expand said glass in said spherical cavity and thereby form a hollow bulb near one end thereof;

(d) discontinuing the application of pressure when glass material blows into the smaller diameter passageway; and (e) removing said tube from said mold.

3. A method according to claim 2 in which said glass is a high quartz glass.

4. A method according to claim 2 including the steps of preheating said mold and said tube prior to insertion of said tube into said mold, and annealing said tube after removal from said mold.

5. A method for removing matter from a patient's upper respiratory tract by suction, which comprises inserting a suction device as claimed in claim 1 into the end of a tracheostomy tube which is outside the patient's body, said suction device being inserted so that said bulb contacts said end of tracheostomy tube, and the opening at the outer end of said projection is in communication with said tracheostomy tube, and applying suction to the end of said suction device which is remote from the bulb.

6. A method as claimed in claim 5 in which said suction is applied by means of a powered vacuum source.

7. A suction device as claimed in claim 1 wherein said bulb is substantially larger in diameter than said projection.

8. A suction device as claimed in claim 1 wherein said projection and said tubular portion are axially aligned.

9. A suction device as claimed in claim 2 wherein the outside diameter of said bulb is greater than 8 mm.

10. A combination as claimed in claim 1 wherein said suction device also comprises a hollow projection of short axial length extending from said bulb in a direction opposite to that of said tubular portion.

11. A suction device according to claim 1 in which the outside diameter of said hollow spherical bulb exceeds eleven (11) millimeters.

12. In combination with a tracheostomy tube, a suction device as claimed in claim 1, that suction device being inserted into the end of said tracheostomy tube which is outside the patient's body so that said spherical bulb is against the end of said tracheostomy tube and the opening in said hollow projection is in communication with said tracheostomy tube, the tubular portion of said suction device being adapted to be attached to a source of vacuum.

* * * * *